United States Patent [19]

Hoey et al.

[11] Patent Number: 5,756,700

[45] Date of Patent: May 26, 1998

[54] NUCLEIC ACID ENCODING HUMAN SIGNAL TRANSDUCER AND ACTIVATOR OF TRANSCRIPTION 4

[75] Inventors: Timothy Hoey, Woodside; Mike Rothe, San Francisco, both of Calif.

[73] Assignee: Tularik Inc., South San Francisco, Calif.

[21] Appl. No.: 839,164

[22] Filed: Apr. 23, 1997

Related U.S. Application Data

[62] Division of Ser. No. 408,318, Mar. 22, 1995, Pat. No. 5,639,858.

[51] Int. Cl.⁶ ................................................. C12N 15/12
[52] U.S. Cl. ..................... 536/23.5; 530/350; 530/324; 530/325; 530/326; 530/327; 530/328; 530/329; 530/330; 530/331
[58] Field of Search ................................ 536/23.1, 23.5; 530/350, 326, 325, 327, 328, 329, 330, 331

[56] References Cited

FOREIGN PATENT DOCUMENTS

| 0367724A1 | 9/1990 | European Pat. Off. |
| 2216418 | 11/1989 | United Kingdom. |
| 2216522 | 11/1989 | United Kingdom. |
| WO/89/07938 | 9/1989 | WIPO. |
| WO/90/08130 | 7/1990 | WIPO. |
| WO/93/00084 | 1/1993 | WIPO. |
| WO/95/09622 | 4/1995 | WIPO. |

OTHER PUBLICATIONS

Patent Abstracts of Japan C–482, p.154, JP 62-223159 (A).
Patent Abstracts of Japan C–685, p. 71, JP 1-287022 (A).
Patent Abstracts of Japan C–561, p. 141, JP 63-230633 (A).

*Primary Examiner*—John Ulm
*Assistant Examiner*—Prema Mertz
*Attorney, Agent, or Firm*—Richard Aron Osman

[57] ABSTRACT

The invention provides methods and compositions relating to interleukin 12 signal transducers, particularly an isolated human signal transducer and activator of transcription 4 (hStat 4), or a fragment thereof having an hStat 4-specific binding affinity, nucleic acids encoding hStat 4, which nucleic acids may be part of hStat 4-expression vectors and may be incorporated into a recombinant cell, agents which selectively bind hStat 4 or hStat 4 intracellular binding targets, or disrupt the binding of hStat 4 to such intracellular targets, methods of making such agents and hStat 4-specific binding targets in the form of cell surface proteins and nucleic acids. An hStat 4 drug screening assay involves forming mixtures of an hStat 4, an intracellular hStat 4 binding target, and a prospective agent at different concentrations. The mixtures are incubated to permit the binding of the intracellular hStat 4 binding target to the hStat 4 and the mixtures are then analyzed for the presence of such binding. A difference in such binding between the first and second mixtures indicates that the agent is capable of modulating the binding of hStat 4 to an intracellular hStat 4 binding target.

40 Claims, No Drawings

5,756,700

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2606 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 82..2324

( i x ) FEATURE:
        ( A ) NAME/KEY: CDS
        ( B ) LOCATION: 82..2328

( x i ) SEQUENCE DESCRIPTION: SEQ ID NO:1:

```
GCTTTCTCCT AGGGACTGTG AGGGGCGCTT CTGACTTTGG ACTTGAGCAC TGCCTGGGAC              60

CTGTGCTGAG AGAGCGCTAG C ATG TCT CAG TGG AAT CAA GTC CAA CAG TTA             111
                       Met Ser Gln Trp Asn Gln Val Gln Gln Leu
                        1               5                  10

GAA ATC AAG TTT TTG GAG CAG GTG GAT CAA TTC TAT GAT GAC AAC TTT             159
Glu Ile Lys Phe Leu Glu Gln Val Asp Gln Phe Tyr Asp Asp Asn Phe
             15                  20                  25

CCC ATG GAA ATT CGG CAT CTG TTG GCC CAA TGG ATT GAA AAT CAA GAC             207
Pro Met Glu Ile Arg His Leu Leu Ala Gln Trp Ile Glu Asn Gln Asp
         30                  35                  40

TGG GAG GCA GCT TCT AAC AAT GAA ACC ATG GCA ACG ATT CTT CTT CAA             255
Trp Glu Ala Ala Ser Asn Asn Glu Thr Met Ala Thr Ile Leu Leu Gln
     45                  50                  55

AAC TTG TTA ATA CAA CTG GAT GAA CAG TTA GGT CGT GTT TCC AAA GAG             303
Asn Leu Leu Ile Gln Leu Asp Glu Gln Leu Gly Arg Val Ser Lys Glu
 60                  65                  70

AAA AAC CTA CTC TTG ATA CAC AAT CTA AAA AGA ATT AGG AAG GTC CTT             351
Lys Asn Leu Leu Leu Ile His Asn Leu Lys Arg Ile Arg Lys Val Leu
 75                  80                  85                  90

CAG GGA AAA TTT CAT GGA AAT CCA ATG CAT GTA GCT GTG GTT ATT TCA             399
Gln Gly Lys Phe His Gly Asn Pro Met His Val Ala Val Val Ile Ser
                 95                 100                 105

AAC TGT TTA AGG GAA GAG AGG AGA ATA TTG GCT GCA GCC AAC ATG CCT             447
Asn Cys Leu Arg Glu Glu Arg Arg Ile Leu Ala Ala Ala Asn Met Pro
             110                 115                 120

GTC CAG GGG CCT CTA GAG AAA TCC TTA CAA AGT TCT TCA GTT TCA GAA             495
Val Gln Gly Pro Leu Glu Lys Ser Leu Gln Ser Ser Ser Val Ser Glu
         125                 130                 135

AGA CAG AGG AAT GTG GAG CAC AAA GTG GCT GCC ATT AAA AAC AGT GTG             543
Arg Gln Arg Asn Val Glu His Lys Val Ala Ala Ile Lys Asn Ser Val
     140                 145                 150

CAG ATG ACA GAA CAA GAT ACC AAA TAC TTA GAA GAT CTG CAA GAC GAA             591
Gln Met Thr Glu Gln Asp Thr Lys Tyr Leu Glu Asp Leu Gln Asp Glu
155                 160                 165                 170

TTT GAC TAC AGG TAT AAA ACA ATT CAG ACA ATG GAT CAG AGT GAC AAG             639
Phe Asp Tyr Arg Tyr Lys Thr Ile Gln Thr Met Asp Gln Ser Asp Lys
                 175                 180                 185

AAT AGT GCC ATG GTG AAT CAG GAA GTT TTG ACA CTG CAG GAA ATG CTT             687
Asn Ser Ala Met Val Asn Gln Glu Val Leu Thr Leu Gln Glu Met Leu
```

-continued

| | | | | | | | | | | | | | | | | |
|---|---|---|---|---|---|---|---|---|---|---|---|---|---|---|---|---|
| | | | | 190 | | | | | 195 | | | | | 200 | | |
| AAC | AGC | CTC | GAT | TTC | AAG | AGA | AAG | GAG | GCT | CTC | AGT | AAA | ATG | ACC | CAA | 735 |
| Asn | Ser | Leu 205 | Asp | Phe | Lys | Arg | Lys 210 | Glu | Ala | Leu | Ser | Lys 215 | Met | Thr | Gln | |
| ATC | ATC | CAT | GAG | ACA | GAC | CTG | TTA | ATG | AAC | ACC | ATG | CTC | ATA | GAA | GAG | 783 |
| Ile | Ile | His 220 | Glu | Thr | Asp | Leu | Leu 225 | Met | Asn | Thr | Met 230 | Leu | Ile | Glu | Glu | |
| CTG | CAA | GAC | TGG | AAG | CGG | CGG | CAG | CAA | ATC | GCC | TGC | ATC | GGG | GGT | CCA | 831 |
| Leu 235 | Gln | Asp | Trp | Lys | Arg 240 | Arg | Gln | Gln | Ile | Ala 245 | Cys | Ile | Gly | Gly | Pro 250 | |
| CTC | CAC | AAT | GGG | CTC | GAC | CAG | CTT | CAG | AAC | TGC | TTT | ACA | CTA | TTG | GCA | 879 |
| Leu | His | Asn | Gly | Leu 255 | Asp | Gln | Leu | Gln | Asn 260 | Cys | Phe | Thr | Leu | Leu 265 | Ala | |
| GAA | AGT | CTT | TTC | CAA | CTG | AGA | AGG | CAA | TTG | GAG | AAA | CTA | GAG | GAG | CAA | 927 |
| Glu | Ser | Leu | Phe 270 | Gln | Leu | Arg | Arg | Gln 275 | Leu | Glu | Lys | Leu | Glu 280 | Glu | Gln | |
| TCT | ACC | AAA | ATG | ACA | TAT | GAA | GGT | GAT | CCC | ATT | CCA | ATG | CAA | AGA | ACT | 975 |
| Ser | Thr | Lys 285 | Met | Thr | Tyr | Glu | Gly 290 | Asp | Pro | Ile | Pro | Met 295 | Gln | Arg | Thr | |
| CAC | ATG | CTA | GAA | AGA | GTC | ACC | TTC | TTG | ATC | TAC | AAC | CTT | TTC | AAG | AAC | 1023 |
| His | Met | Leu 300 | Glu | Arg | Val | Thr | Phe 305 | Leu | Ile | Tyr | Asn | Leu 310 | Phe | Lys | Asn | |
| TCA | TTT | GTG | GTT | GAG | CGA | CAG | CCA | TGT | ATG | CCA | ACC | CAC | CCT | CAG | AGG | 1071 |
| Ser 315 | Phe | Val | Val | Glu | Arg 320 | Gln | Pro | Cys | Met | Pro 325 | Thr | His | Pro | Gln | Arg 330 | |
| CCG | TTG | GTA | CTT | AAA | ACC | CTA | ATT | CAG | TTC | ACT | GTA | AAA | CTA | AGG | CTA | 1119 |
| Pro | Leu | Val | Leu | Lys 335 | Thr | Leu | Ile | Gln | Phe 340 | Thr | Val | Lys | Leu | Arg 345 | Leu | |
| CTA | ATA | AAA | TTG | CCA | GAA | CTA | AAC | TAT | CAG | GTA | AAG | GTT | AAG | GCA | TCA | 1167 |
| Leu | Ile | Lys | Leu 350 | Pro | Glu | Leu | Asn | Tyr 355 | Gln | Val | Lys | Val | Lys 360 | Ala | Ser | |
| ATT | GAC | AAG | AAT | GTT | TCA | ACT | CTA | AGC | AAC | CGA | AGA | TTT | GTA | CTT | TGT | 1215 |
| Ile | Asp | Lys 365 | Asn | Val | Ser | Thr | Leu 370 | Ser | Asn | Arg | Arg | Phe 375 | Val | Leu | Cys | |
| GGA | ACT | AAT | GTC | AAA | GCC | ATG | TCT | ATT | GAA | GAA | TCT | TCC | AAT | GGG | AGT | 1263 |
| Gly | Thr | Asn 380 | Val | Lys | Ala | Met | Ser 385 | Ile | Glu | Glu | Ser | Ser 390 | Asn | Gly | Ser | |
| CTC | TCA | GTA | GAA | TTT | CGA | CAT | TTG | CAA | CCA | AAG | GAA | ATG | AAG | TCC | AGT | 1311 |
| Leu 395 | Ser | Val | Glu | Phe | Arg 400 | His | Leu | Gln | Pro | Lys 405 | Glu | Met | Lys | Ser | Ser 410 | |
| GCT | GGA | GGT | AAA | GGA | AAT | GAG | GGC | TGT | CAC | ATG | GTG | ACT | GAA | GAA | CTT | 1359 |
| Ala | Gly | Gly | Lys | Gly 415 | Asn | Glu | Gly | Cys | His 420 | Met | Val | Thr | Glu | Glu 425 | Leu | |
| CAT | TCC | ATA | ACG | TTT | GAA | ACA | CAG | ATC | TGC | CTC | TAT | GGC | CTG | ACC | ATA | 1407 |
| His | Ser | Ile | Thr 430 | Phe | Glu | Thr | Gln | Ile 435 | Cys | Leu | Tyr | Gly | Leu 440 | Thr | Ile | |
| GAT | TTG | GAG | ACC | AGC | TCA | TTG | CCT | GTG | GTG | ATG | ATT | TCC | AAT | GTC | AGT | 1455 |
| Asp | Leu | Glu 445 | Thr | Ser | Ser | Leu | Pro 450 | Val | Val | Met | Ile | Ser 455 | Asn | Val | Ser | |
| CAG | TTA | CCT | AAT | GCT | TGG | GCA | TCC | ATC | ATT | TGG | TAC | AAC | GTG | TCA | ACC | 1503 |
| Gln | Leu | Pro 460 | Asn | Ala | Trp | Ala 465 | Ser | Ile | Ile | Trp | Tyr 470 | Asn | Val | Ser | Thr | |
| AAC | GAT | TCC | CAG | AAC | TTG | GTT | TTC | TTT | AAT | AAT | CCT | CCA | CCT | GCC | ACA | 1551 |
| Asn 475 | Asp | Ser | Gln | Asn | Leu 480 | Val | Phe | Phe | Asn | Asn 485 | Pro | Pro | Pro | Ala | Thr 490 | |
| TTG | AGT | CAA | CTA | CTG | GAG | GTG | ATG | AGC | TGG | CAG | TTT | TCA | TCG | TAC | GTT | 1599 |
| Leu | Ser | Gln | Leu | Glu 495 | Glu | Val | Met | Ser | Trp 500 | Gln | Phe | Ser | Ser | Tyr 505 | Val | |
| GGT | CGT | GGT | CTT | AAC | TCA | GAT | CAA | CTC | CAT | ATG | CTG | GCA | GAG | AAG | CTT | 1647 |
| Gly | Arg | Gly | Leu | Asn | Ser | Asp | Gln | Leu | His | Met | Leu | Ala | Glu | Lys | Leu | |

| | | | | | | | | | | | | | | | | |
|---|---|---|---|---|---|---|---|---|---|---|---|---|---|---|---|---|
| | | 510 | | | | | 515 | | | | | 520 | | | | |
| ACA | GTC | CAA | TCT | AGC | TAC | AGT | GAT | GGT | CAC | CTC | ACC | TGG | GCC | AAG | TTC | 1695 |
| Thr | Val | Gln | Ser | Ser | Tyr | Ser | Asp | Gly | His | Leu | Thr | Trp | Ala | Lys | Phe | |
| | | 525 | | | | | 530 | | | | | 535 | | | | |
| TGC | AAG | GAA | CAT | TTA | CCT | GGT | AAA | TCA | TTT | ACC | TTT | TGG | ACA | TGG | CTT | 1743 |
| Cys | Lys | Glu | His | Leu | Pro | Gly | Lys | Ser | Phe | Thr | Phe | Trp | Thr | Trp | Leu | |
| | 540 | | | | | 545 | | | | | 550 | | | | | |
| GAA | GCA | ATA | TTG | GAT | CTA | ATT | AAG | AAA | CAC | ATT | CTT | CCC | CTT | TGG | ATT | 1791 |
| Glu | Ala | Ile | Leu | Asp | Leu | Ile | Lys | Lys | His | Ile | Leu | Pro | Leu | Trp | Ile | |
| 555 | | | | | 560 | | | | | 565 | | | | | 570 | |
| GAT | GGG | TAT | GTC | ATG | GGC | TTT | GTT | AGC | AAA | GAG | AAG | GAA | CGG | CTG | TTG | 1839 |
| Asp | Gly | Tyr | Val | Met | Gly | Phe | Val | Ser | Lys | Glu | Lys | Glu | Arg | Leu | Leu | |
| | | | | 575 | | | | | 580 | | | | | 585 | | |
| CTA | AAG | GAT | AAA | ATG | CCT | GGC | ACC | TTT | TTA | TTA | AGA | TTC | AGT | GAA | AGC | 1887 |
| Leu | Lys | Asp | Lys | Met | Pro | Gly | Thr | Phe | Leu | Leu | Arg | Phe | Ser | Glu | Ser | |
| | | | 590 | | | | | 595 | | | | | 600 | | | |
| CAT | CTC | GGA | GGA | ATA | ACT | TTC | ACC | TGG | GTG | GAC | CAT | TCT | GAA | AGT | GGG | 1935 |
| His | Leu | Gly | Gly | Ile | Thr | Phe | Thr | Trp | Val | Asp | His | Ser | Glu | Ser | Gly | |
| | | 605 | | | | | 610 | | | | | 615 | | | | |
| GAA | GTG | AGA | TTC | CAC | TCT | GTA | GAA | CCC | TAC | AAT | AAA | GGC | CGG | TTG | TCT | 1983 |
| Glu | Val | Arg | Phe | His | Ser | Val | Glu | Pro | Tyr | Asn | Lys | Gly | Arg | Leu | Ser | |
| | 620 | | | | | 625 | | | | | 630 | | | | | |
| GCT | CTG | CCA | TTC | GCT | GAC | ATC | CTG | CGA | GAC | TAC | AAA | GTT | ATT | ATG | GCT | 2031 |
| Ala | Leu | Pro | Phe | Ala | Asp | Ile | Leu | Arg | Asp | Tyr | Lys | Val | Ile | Met | Ala | |
| 635 | | | | | 640 | | | | | 645 | | | | | 650 | |
| GAA | AAC | ATT | CCT | GAA | AAC | CCT | CTG | AAG | TAC | CTA | TAT | CCT | GAC | ATT | CCC | 2079 |
| Glu | Asn | Ile | Pro | Glu | Asn | Pro | Leu | Lys | Tyr | Leu | Tyr | Pro | Asp | Ile | Pro | |
| | | | | 655 | | | | | 660 | | | | | 665 | | |
| AAA | GAC | AAA | GCC | TTC | GGT | AAA | CAC | TAC | AGC | TCT | CAG | CCT | TGC | GAA | GTT | 2127 |
| Lys | Asp | Lys | Ala | Phe | Gly | Lys | His | Tyr | Ser | Ser | Gln | Pro | Cys | Glu | Val | |
| | | | 670 | | | | | 675 | | | | | 680 | | | |
| TCA | AGA | CCA | ACA | GAA | AGG | GGT | GAC | AAA | GGT | TAT | GTT | CCT | TCT | GTT | TTT | 2175 |
| Ser | Arg | Pro | Thr | Glu | Arg | Gly | Asp | Lys | Gly | Tyr | Val | Pro | Ser | Val | Phe | |
| | | 685 | | | | | 690 | | | | | 695 | | | | |
| ATC | CCC | ATC | TCA | ACA | ATC | CGA | AGT | GAT | TCA | ACA | GAG | CCA | CAT | TCT | CCA | 2223 |
| Ile | Pro | Ile | Ser | Thr | Ile | Arg | Ser | Asp | Ser | Thr | Glu | Pro | His | Ser | Pro | |
| | 700 | | | | | 705 | | | | | 710 | | | | | |
| TCA | GAC | CTT | CTT | CCC | ATG | TCT | CCA | AGT | GTG | TAT | GCG | GTG | TTG | AGA | GAA | 2271 |
| Ser | Asp | Leu | Leu | Pro | Met | Ser | Pro | Ser | Val | Tyr | Ala | Val | Leu | Arg | Glu | |
| 715 | | | | | 720 | | | | | 725 | | | | | 730 | |
| AAC | CTG | AGT | CCC | ACA | ACA | ATT | GAA | ACT | GCA | ATG | AAG | TCT | CCT | TAT | TCT | 2319 |
| Asn | Leu | Ser | Pro | Thr | Thr | Ile | Glu | Thr | Ala | Met | Lys | Ser | Pro | Tyr | Ser | |
| | | | | 735 | | | | | 740 | | | | | 745 | | |
| GCT | GAA | TGA | CAGGATAAAC | TCTGACGCAC | CAAGAAGGA | AGCAAATGAA | | | | | | | | | | 2368 |
| Ala | Glu | * | | | | | | | | | | | | | | |
| AAAGTTTAAA | GACTGTTCTT | TGCCCAATAA | CCACATTTTA | TTTCTTCAGC | TTTGTAAATA | | | | | | | | | | | 2428 |
| CCAGGTTCTA | GGAAATGTTT | GACATCTGAA | GCTCTCTTCA | CACTCCCGTG | GCACTCCTCA | | | | | | | | | | | 2488 |
| ATTGGGAGTG | TTGTGACTGA | AATGCTTGAA | ACCAAAGCTT | CAGATAAACT | TGCAAGATAA | | | | | | | | | | | 2548 |
| GACAACTTTA | AGAAACCAGT | GTTAATAACA | ATATTAACAG | AAAAAAAAAA | AAAAAAA | | | | | | | | | | | 2606 |

( 2 ) INFORMATION FOR SEQ ID NO:2:

( i ) SEQUENCE CHARACTERISTICS:
    ( A ) LENGTH: 748 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Ser Gln Trp Asn Gln Val Gln Gln Leu Glu Ile Lys Phe Leu Glu
 1           5                    10                  15
Gln Val Asp Gln Phe Tyr Asp Asp Asn Phe Pro Met Glu Ile Arg His
            20                  25                  30
Leu Leu Ala Gln Trp Ile Glu Asn Gln Asp Trp Glu Ala Ala Ser Asn
        35                  40                  45
Asn Glu Thr Met Ala Thr Ile Leu Leu Gln Asn Leu Leu Ile Gln Leu
    50                  55                  60
Asp Glu Gln Leu Gly Arg Val Ser Lys Glu Lys Asn Leu Leu Leu Ile
65                  70                  75                  80
His Asn Leu Lys Arg Ile Arg Lys Val Leu Gln Gly Lys Phe His Gly
                85                  90                  95
Asn Pro Met His Val Ala Val Val Ile Ser Asn Cys Leu Arg Glu Glu
            100                 105                 110
Arg Arg Ile Leu Ala Ala Ala Asn Met Pro Val Gln Gly Pro Leu Glu
        115                 120                 125
Lys Ser Leu Gln Ser Ser Ser Val Ser Glu Arg Gln Arg Asn Val Glu
    130                 135                 140
His Lys Val Ala Ala Ile Lys Asn Ser Val Gln Met Thr Glu Gln Asp
145                 150                 155                 160
Thr Lys Tyr Leu Glu Asp Leu Gln Asp Glu Phe Asp Tyr Arg Tyr Lys
                165                 170                 175
Thr Ile Gln Thr Met Asp Gln Ser Asp Lys Asn Ser Ala Met Val Asn
            180                 185                 190
Gln Glu Val Leu Thr Leu Gln Glu Met Leu Asn Ser Leu Asp Phe Lys
        195                 200                 205
Arg Lys Glu Ala Leu Ser Lys Met Thr Gln Ile Ile His Glu Thr Asp
    210                 215                 220
Leu Leu Met Asn Thr Met Leu Ile Glu Glu Leu Gln Asp Trp Lys Arg
225                 230                 235                 240
Arg Gln Gln Ile Ala Cys Ile Gly Gly Pro Leu His Asn Gly Leu Asp
                245                 250                 255
Gln Leu Gln Asn Cys Phe Thr Leu Leu Ala Glu Ser Leu Phe Gln Leu
            260                 265                 270
Arg Arg Gln Leu Glu Lys Leu Glu Glu Gln Ser Thr Lys Met Thr Tyr
        275                 280                 285
Glu Gly Asp Pro Ile Pro Met Gln Arg Thr His Met Leu Glu Arg Val
    290                 295                 300
Thr Phe Leu Ile Tyr Asn Leu Phe Lys Asn Ser Phe Val Val Glu Arg
305                 310                 315                 320
Gln Pro Cys Met Pro Thr His Pro Gln Arg Pro Leu Val Leu Lys Thr
                325                 330                 335
Leu Ile Gln Phe Thr Val Lys Leu Arg Leu Leu Ile Lys Leu Pro Glu
            340                 345                 350
Leu Asn Tyr Gln Val Lys Val Lys Ala Ser Ile Asp Lys Asn Val Ser
        355                 360                 365
Thr Leu Ser Asn Arg Arg Phe Val Leu Cys Gly Thr Asn Val Lys Ala
    370                 375                 380
Met Ser Ile Glu Glu Ser Ser Asn Gly Ser Leu Ser Val Glu Phe Arg
385                 390                 395                 400
His Leu Gln Pro Lys Glu Met Lys Ser Ser Ala Gly Gly Lys Gly Asn
                405                 410                 415
Glu Gly Cys His Met Val Thr Glu Glu Leu His Ser Ile Thr Phe Glu
            420                 425                 430
```

Thr Gln Ile Cys Leu Tyr Gly Leu Thr Ile Asp Leu Glu Thr Ser Ser
        435                 440                 445
Leu Pro Val Val Met Ile Ser Asn Val Ser Gln Leu Pro Asn Ala Trp
    450                 455                 460
Ala Ser Ile Ile Trp Tyr Asn Val Ser Thr Asn Asp Ser Gln Asn Leu
465                 470                 475                 480
Val Phe Phe Asn Asn Pro Pro Pro Ala Thr Leu Ser Gln Leu Leu Glu
                485                 490                 495
Val Met Ser Trp Gln Phe Ser Ser Tyr Val Gly Arg Gly Leu Asn Ser
            500                 505                 510
Asp Gln Leu His Met Leu Ala Glu Lys Leu Thr Val Gln Ser Ser Tyr
        515                 520                 525
Ser Asp Gly His Leu Thr Trp Ala Lys Phe Cys Lys Glu His Leu Pro
    530                 535                 540
Gly Lys Ser Phe Thr Phe Trp Thr Trp Leu Glu Ala Ile Leu Asp Leu
545                 550                 555                 560
Ile Lys Lys His Ile Leu Pro Leu Trp Ile Asp Gly Tyr Val Met Gly
                565                 570                 575
Phe Val Ser Lys Glu Lys Glu Arg Leu Leu Leu Lys Asp Lys Met Pro
            580                 585                 590
Gly Thr Phe Leu Leu Arg Phe Ser Glu Ser His Leu Gly Gly Ile Thr
        595                 600                 605
Phe Thr Trp Val Asp His Ser Glu Ser Gly Glu Val Arg Phe His Ser
    610                 615                 620
Val Glu Pro Tyr Asn Lys Gly Arg Leu Ser Ala Leu Pro Phe Ala Asp
625                 630                 635                 640
Ile Leu Arg Asp Tyr Lys Val Ile Met Ala Glu Asn Ile Pro Glu Asn
                645                 650                 655
Pro Leu Lys Tyr Leu Tyr Pro Asp Ile Pro Lys Asp Lys Ala Phe Gly
            660                 665                 670
Lys His Tyr Ser Ser Gln Pro Cys Glu Val Ser Arg Pro Thr Glu Arg
        675                 680                 685
Gly Asp Lys Gly Tyr Val Pro Ser Val Phe Ile Pro Ile Ser Thr Ile
    690                 695                 700
Arg Ser Asp Ser Thr Glu Pro His Ser Pro Ser Asp Leu Leu Pro Met
705                 710                 715                 720
Ser Pro Ser Val Tyr Ala Val Leu Arg Glu Asn Leu Ser Pro Thr Thr
                725                 730                 735
Ile Glu Thr Ala Met Lys Ser Pro Tyr Ser Ala Glu
            740                 745

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTATTTCCCA GAAAAGGAAC          20

( 2 ) INFORMATION FOR SEQ ID NO:4:

( i ) SEQUENCE CHARACTERISTICS:

( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GTATCACCCA GTCAAGGAAC     20

1

NUCLEIC ACID ENCODING HUMAN SIGNAL TRANSDUCER AND ACTIVATOR OF TRANSCRIPTION 4

This is a division, of application Ser. No. 08/408,318 filed Mar. 22, 1995 now U.S. Pat. No. 5,639,858.

INTRODUCTION

1. Field of the Invention

The field of this invention is the human interleukin-12 signal transducter and activator of transcription.

2. Background

Identifying and developing new pharmaceuticals is a multibillion dollar industry in the U.S. alone. Gene specific transcription factors provide a promising class of targets for novel therapeutics directed to these and other human diseases. Urgently needed are efficient methods of identifying pharmacological agents or drugs which are active at the level of gene transcription. Methods amenable to automated, cost-effective, high throughput drug screening have immediate application in a broad range of domestic and international pharmaceutical and biotechnology drug development programs.

Interleukin-12 (IL-12) is an immunomodulatory cytokine secreted by macrophages, activated monocytes and B-cells. IL-12 is an important regulator of the effector phase of cell-mediated immunity, providing a crucial link in immune system surveillance for cellular infection, transformation, etc. For example, IL-12 is the most potent NK cell stimulator known. IL-12 stimulates the differentiation of naive CD4+T cells to the TH1 subset, and stimulates the differentiation of CD8+T cells into mature, functionally active CTLs.

As such, IL-12 signal transduction provides an important target for pharmaceutical intervention in the immune system, especially autoimmunity. Accordingly, it is desired to identify agents which specifically interfere with transduction of IL-12 signalling. Unfortunately, the reagents necessary for the development of high-throughput screening assays for such therapeutics are unavailable.

3. Relevant Literature

A subunit of the IL-12 receptor is described in Chua et al. (1994) J. Immunol 153, 128–136. Yamamoto et al (1994) Mol and Cell Biol 14:4342–4349 and Zhong et al. (1994) 91:4806–4810 disclose a mouse protein, mStat 4, with sequence similarity to hStat 4.

SUMMARY OF THE INVENTION

The invention provides methods and compositions relating to interleukin-12 signal transducers. In one embodiment, the invention provides isolated human signal transducer and activator of transcription 4 (hStat 4), or a fragment thereof having an hStat 4-specific binding affinity. The invention provides nucleic acids encoding the subject hStat 4 and hStat 4 fragments, which nucleic acids may be part of hStat 4-expression vectors and may be incorporated into a recombinant cell. The invention provides agents which selectively bind hStat 4 or hStat 4 intracellular binding targets, or disrupt the binding of hStat 4 to such intracellular targets, and methods of maling such agents. The invention also provides specific hStat 4 binding targets in the form of cell surface proteins and nucleic acids.

The subject hStat 4 and hStat 4 fragments and find particular use in screening assays for agents or lead compounds for agents useful in the diagnosis, prognosis or treatment of disease, particularly disease associated with undesirable cell growth, differentiation and/or cytokine signal responsiveness. One such assay involves forming mixtures of an hStat 4, an intracellular hStat 4 binding target, and a prospective agent at different concentrations. Typically, one mixture is a negative control (i.e. the agent concentration is zero). The mixtures are incubated to permit the binding of the intracellular hStat 4 binding target to the hStat 4 and the mixtures are then analyzed for the presence of such binding. A difference in such binding between the first and second mixtures indicates that the agent is capable of modulating the binding of hStat 4 to an intracellular hStat 4 binding target.

DETAILED DESCRIPTION OF THE INVENTION

The invention provides methods and compositions relating to human interleukin-12 signal transducers including hStat 4. A cDNA encoding hStat 4 and its translation product are shown in SEQUENCE ID NOS: 1 and 2, respectively.

The subject hStat 4 fragments have one or more hStat 4-specific binding affinities which distinguish other Stats, including the ability to specifically bind at least one natural human intracellular hStat 4-specific binding target or a hStat 4-specific binding agent such as a hStat 4-specific antibody or a hStat 4-specific binding agent identified in assays such as described below. Accordingly, the specificity of hStat 4 fragment specific binding agents is confirmed by ensuring non-crossreactivity with other Stats including murine stat 4. Furthermore, preferred hStat 4 fragments are capable of eliciting an antibody capable of distinguishing hStat 4 from other Stats and mStat 4. Methods for making immunogenic peptides through the use of conjugates, adjuvants, etc. and methods for eliciting antibodies, e.g. immunizing rabbits, are well known.

Exemplary natural intracellular binding targets include nucleic acids which comprise one or more hStat 4 DNA binding sites such as the interleukin response element of the gene encoding FcγRI, cell surface proteins such as the hStat 4 binding domain the IL-12 receptor and phosphotryrosine peptide fragments thereof, protein kinases such as Janus tyrosine kinases, transcription factors such as those comprising the transcription initiation complex, etc., and fragments of such targets which are capable of hStat 4-specific binding. Other natural hStat 4 binding targets are readily identified by screening cells, membranes and cellular extracts and fractions with the disclosed materials and methods and by other methods known in the art. For example, two-hybrid screening using hStat 4 fragments are used to identify intracellular targets which specifically bind such fragments. Preferred hStat 4 fragments retain the ability to specifically bind at least one of an hStat 4 DNA binding site and an intracellular domain of an IL-12 receptor subunit. For example, using a strategy analagous to that described in Hou et al. (1994) Science 265: 1701–1706, carboxyl terminus IL-12 receptor phosphotyrosine peptides are shown to inhibit hStat 4 DNA binding. IL-12 receptor variants lacking these two peptides are found to lose the ability to activate Stat proteins. Convenient ways to verify the ability of a given hStat 4 fragment to specifically bind such targets include in vitro labelled binding assays such as described below, and EMSAs.

A wide variety of molecular and biochemical methods are available for generating and expressing hStat 4 fragments, see e.g. Molecular Cloning. A Laboratory Manual (2nd Ed., Sambrook, Fritsch and Maniatis. Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, hStat 4 or fragments thereof may be obtained by chemical synthesis, expression in bacteria such as *E. coli* and eukaryotes such as yeast or vaccinia or baculovirus-based expression systems, etc., depending on the size, nature and quantity of the hStat 4 or fragment. The subject hStat 4 fragments are of length sufficient to provide a novel peptide. As used herein, such peptides are at least 5, usually at least about 6, more usually at least about 8, most usually at least about 10 amino acids. hStat 4 fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

The subject hStat 4 fragments maintain binding affinity of not less than six, preferably not less than four, more preferably not less than two orders of magnitude less than the binding equilibrium constant of a full-length native hStat 4 to the binding target under similar conditions. Particular hStat 4' fragments or deletion mutants are shown to function in a dominant-negative fashion. HStat 4 fragments containing tyrosine residue 693 is also shown to prevent tyrosine phosphorylation of hStat 4 thereby inhibiting hStat 4 activity. Such fragments provide therapeutic agents, e.g. when delivered by intracellular immunization—transfection of susceptible cells with nucleic acids encoding such mutants.

The claimed hStat 4 and hStat 4 fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample.

The invention provides hStat 4-specific binding agents, methods of identifying and making such agents, and their use in diagnosis, therapy and pharmaceutical development. For example, hStat 4-specific agents are useful in a variety of diagnostic applications, especially where disease or disease prognosis is associated with immune disfunction resulting from improper expression of hStat 4. Novel hStat 4-specific binding agents include hStat 4-specific antibodies; novel nucleic acids with sequence similarity to that of the Fc-yRI receptor promoter as described below; isolated IL-12 receptor subunit domains; other natural intracellular binding agents identified with assays such as one- and two-hybrid screens; non-natural intracellular binding agents identified in screens of chemical libraries, etc.

Generally, hStat 4-specificity of the binding target is shown by binding equilibrium constants. Such targets are capable of selectively binding a hStat 4, i.e. with an equilibrium constant at least about $10^7 M^{-1}$, preferably at least about $10^8 M^{-1}$, more preferably at least about $10^9 M^{-1}$. A wide variety of cell-based and cell-free assays may be used to demonstrate hStat 4-specific binding. Cell based assays include one and two-hybrid screens, mediating or competitively inhibiting hStat 4-mediated transcription, etc. Preferred are rapid in vitro, cell-free assays such as mediating or inhibiting hStat 4-protein (e.g. hStat 4-IL-12 receptor subunit binding), hStat 4-nucleic acid binding, immunoassays, etc. Other useful screening assays for hStat 4/hStat 4 fragment-target binding include fluorescence resonance energy transfer (FRET), electrophoretic mobility shift analysis (EMSA), etc.

The invention also provides nucleic acids encoding the subject hStat 4 and hStat 4 fragments, which nucleic acids may be part of hStat 4-expression vectors and may be incorporated into recombinant cells for expression and screening, transgenic animals for functional studies (e.g. the efficacy of candidate drugs for disease associated with expression of a hStat 4), etc. In addition, the invention provides nucleic acids sharing substantial sequence similarity with that of one or more wild-type hStat 4 nucleic acids. Substantially identical or homologous nucleic acid sequences hybridize to their respective complements under high stringency conditions, for example, at 55° C. and hybridization buffer comprising 50% formamide in 0.9M saline/0.09M sodium citrate (SSC) buffer and remain bound when subject to washing at 55° C. with the SSCIformamide buffer. Where the sequences diverge, the differences are preferably silent, i.e. or a nucleotide change providing a redundant codon, or conservative, i.e. a nucleotide change providing a conservative amino acid substitution.

The subject nucleic acids find a wide variety of applications including use as hybridization probes, PCR primers, therapeutic nucleic acids, etc. for use in detecting the presence of hStat 4 genes and gene transcripts, for detecting or amplifying nucleic acids with substantial sequence similarity such as hStat 4 homologs and structural analogs, and for gene therapy applications. Given the subject probes, materials and methods for probing cDNA and genetic libraries and recovering homologs are known in the art. Preferred libraries are derived from human immune cells, especially cDNA libraries from differentiated and activated human lymphoid cells. In one application, the subject nucleic acids find use as hybridization probes for identifying hStat 4 cDNA homologs with substantial sequence similarity. These homologs in turn provide additional Stats and Stat fragment for use in binding assays and therapy as described herein. hStat 4 encoding nucleic acids also find applications in gene therapy. For example, nucleic acids encoding dominant-negative hStat 4 mutants are cloned into a virus and the virus used to transfect and confer disease (e.g. autoimmune disease) resistance to the transfected cells.

Therapeutic hStat 4 nucleic acids are used to modulate, usually reduce, cellular expression or intracellular concentration or availability of active hStat 4. These nucleic acids are typically antisense: single-stranded sequences comprising complements of the disclosed hStat 4 nucleic acids. Antisense modulation of hStat 4 expression may employ hStat 4 antisense nucleic acids operably linked to gene regulatory sequences. Cell are transfected with a vector comprising an hStat 4 sequence with a promoter sequence oriented such that transcription of the gene yields an anti-sense transcript capable of binding to endogenous hStat 4 encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a hStat 4 or hStat 4 fragment may be administered to the target cell, in or temporarily isolated from a host, at a concentration that results in a substantial reduction in hStat 4 expression. For gene therapy involving the transfusion of hStat 4 transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The subject nucleic acids are often recombinant, meaning they comprise a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of hStat 4 modulatable cellular function, particularly hStat 4 mediated interleukin signal transduction. Generally, these screening methods involve assaying for compounds which interfere with hStat 4 activity such as hStat 4-IL-12 receptor binding, hStat 4-DNA binding, etc. The methods are amenable to automated, cost-effective high throughput drug screening and have immediate application in a broad range of domestic and international pharmaceutical and biotechnology drug development programs.

Target therapeutic indications are limited only in that the target cellular function (e.g. gene expression) be subject to modulation, usually inhibition, by disruption of the formation of a complex (e.g. transcription complex) comprising a hStat 4 or hStat 4 fragment and one or more natural hStat 4 intracellular binding targets. Since a wide variety of genes are subject to hStat 4 regulated gene transcription, target indications may include viral, bacterial and fungal infections, metabolic disease, genetic disease, cell growth and regulatory disfunction, such as neoplasia, inflammation, hypersensitivity, etc. Frequently, the target indication is related to either immune dysfunction or selective immune suppression.

A wide variety of assays for binding agents are provided including labelled in vitro protein-protein and protein-DNA binding assay, electrophoretic mobility shift assays, immunoassays for protein binding or transcription complex formation, cell based assays such as one, two and three hybrid screens, expression assays such as transcription assays, etc. For example, three-hybrid screens are used to rapidly examine the effect of transfected nucleic acids, which may, for example, encode combinatorial peptide libraries or antisense molecules, on the intracellular binding of hStat 4 or hStat 4 fragments to intracellular hStat 4 targets. Convenient reagents for such assays (e.g. GAL4 fusion partners) are known in the art. hStat 4 or hStat 4 fragments used in the methods are usually added in an isolated, partially pure or pure form and are typically recombinantly produced. The hStat 4 or fragment may be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural intracellular hStat 4 binding target such as an IL-12 receptor, subunit domain or a nucleic acid comprising a sequence which shares sufficient sequence similarity with a gene or gene regulatory region to which the native hStat 4 naturally binds to provide sequence-specific binding of the hStat 4 or hStat 4 fragment. Such a nucleic acid may further comprise one or more sequences which facilitate the binding of a second transcription factor or fragment thereof which cooperatively binds the nucleic acid with the hStat 4 (i.e. at least one increases the affinity or specificity of the DNA binding of the other). While native binding targets may be used, it is frequently preferred to use portions (e.g. peptides, nucleic acid fragments) or analogs (i.e. agents which mimic the hStat 4 binding properties of the natural binding target for the purposes of the assay) thereof so long as the portion provides binding affinity and avidity to the hStat 4 conveniently measurable in the assay. Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art. In addition, other high affinity natural and non-natural DNA binding sites may be generated by known methods, e.g. Blackwell and Weintraub (1990) Science 25: 1104–1110.

The hStat 4 fragment is selected to provide specific binding to the selected intracellular binding target. For example, where the target is the IL-12 receptor or receptor portion, the hStat 4 fragment will generally include the SH2 domain (residues 569–668).

Where used, the nucleic acid portion bound by the peptide (s) may be continuous or segmented and is usually linear and double-stranded DNA, though circular plasmids or other nucleic acids or structural analogs may be substituted so long as hStat 4 sequence-specific binding is retained. In some applications, supercoiled DNA provides optimal sequence-specific binding and is preferred. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp. Additional nucleotides may be used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the hStat 4 specifically binds the cellular binding target, portion or analog. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the hStat 4 and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. For cell based assays such as one, two, and three hybrid screens, the transcript resulting from hStat 4-target binding usually encodes a directly or indirectly detectable product (e.g. galactosidase activity, luciferase activity, etc.). For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit hStat 4 - target binding or transcription complex formation provide valuable reagents to the pharmaceutical industries for animal and human trials.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing the subject hStat 4 and hStat 4 fragments.

The subject hStat 4 and hStat 4 fragments and nucleic acids provide a wide variety of uses in addition to the in vitro binding assays described above. For example, cell-based assays are provided which involve transfecting an IL-12 receptor subunit or functional fragment thereof expressing cell with an hStat 4 inducible reporter such as luciferase. Agents which modulate hStat 4 mediated cell function are then detected through a change in the reporter. Another approach is a transient expression assay. In this method, cells are transfected with one or more constructs encoding in sum, a polypeptide comprising a portion of hStat 4 capable of selectively binding an natural IL-12 receptor target and a reporter under the transcriptional control of a promoter comprising a functional hStat 4 binding site. The cell may advantageously also be cotransfected with a construct encoding an hStat 4 activator, usually a tyrosine kinase, particularly a Jak kinase.

The subject compositions also provide therapeutic applications. For example, hStat 4 peptides comprising IL-12 receptor, DNA or transcription factor interaction domains or IL-12 receptor peptides capable of selectively binding said hStat 4 peptides find use in treating disease associated with undesirable cell growth, differentiation, particularly immune cell differentiation, and cytokine, particularly interleukin, more particularly IL-12, responsiveness. For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 µg/kg of the recipient. For peptide agents, the concentration of will generally be in the range of about 100 to 500 µg/ml in the dose administered. Other additives may be included, such as stabilizers, bactericides, etc. These additives will be present in conventional amounts.

The following examples are offered by way of illustration and not by way of limitation.

EXPERIMENTAL

Immunodepletion, Supershifting and Oligonucleotide Competition Assays:

Protein:DNA complexes were visualized by a gel mobility shift assay under non-denaturing conditions. Specificity of protein:DNA interaction was tested using 100-fold molar excess of either the native FcgRI probe (5'-GTATrTCCCAGAAAAGGAAC-3', SEQUENCE ID NO: 3) or the mutated derivative (5'-GTATCACCCAG TCAAGGAAC-3', SEQUENCE ID NO: 4). Antibody supershift experiments were performed by incubating protein samples with antibodies (Santa Cruz Biotech) for 30 minutes at 4° C. prior to exposure to the FcgRI DNA probe. Proteins purified from YT cells were purged of Stat 1, Stat 3 and Stat 4 by immunodepletion. 500 mg of each antibody (specific to Stat 1, Stat 3 and Stat 4) were incubated for 2 hours at room temperature with a slurry of protein-A Sepharose beads (Pharmacia) sufficient to yield 100ml of bed column. Beads were washed three times with 1 ml of buffer C and then incubated for 2 hours at room temperature with Stat proteins purified from IL-12 induced YT cells. Beads were recovered by centrifugation and washed three times with 1 ml of buffer C. Unbound, wash and bound fractions were recovered and subjected to SDS-gel electrophoresis for subsequent staining with Coomassie blue, anti-phosphotyrosine antibodies and Stat antibodies.

Cloning of hStat 4 cDNA:

In order to clone human STAT4 cDNAs, oligonucleotides were designed for PCR. The goal was to obtain a fragment that would specifically hybridize hSTAT4 yet none of the other members of the STAT family. Employing manual and computer-assisted sequence alignments of existing STAT cDNA, we attempted to identify regions combining high STAT divergence and low codon degeneracy for primer design, flanking a region optimized for effective library hybridization. The primer designs ultimately selected for use are indicated below. The degenerate positions are indicated by lower case letters separated by slashes.

MR15=TTc/t CAc/t GGg/a/t/c AAc/t CCg/a/t/c ATG CA

MR16=TT c/tTT g/aTC g/a/t/cCC TG a/g TC CAT

MR17=TC g/aTT g/a/t/c AC g/a/t/cAT t/cTG g/a/t/cGT CAT

MR15 corresponds to amino acids 94–100. MR16 is the reverse complement of amino acids 181–187. MR17 is the reverse complement of 216–222. Reverse transcriptase and polymerase chain reactions were carried out with polyA+ RNA from the human T cell line Jurkat as described below.

9.5 ml $H_2O$; 2.0 ml mRNA; 1.0 ml oligo dT primer

65° C. 12 min.; 22° C. 2 min.

1 ml RNAse inhibitor; 4 ml 5× RT buffer; 1 ml 100 mM dNTPs; 1 ml sodium; pyrophosphate; 0.5 ml Reverse Transcriptase 42° C. 60 min.; 95° C. 3 min.

50 ml Polymerase Chain Reactions were set up as follows:

29 ml $H_2O$; 5 ml 10× buffer (100 mM TRIS pH 8.3, 50 mM KCl); 3 ml 25 mM $MgCl_2$; 1.5 ml each primer; 1.5 ml DNA (from reverse transcription reaction); 1 ml Taq poymerase (diluted 1:4)

6 min 95° C.; 35 cycles of 95° C. 45 sec; 55° C. 1 min; 72° C. 3 min.

The combination of MR15 and MR16 yielded a product of the correct size of approximately 280 bp. This fragment was subcloned, sequenced, and confirmed to be derived from the human STAT4 gene. The combination of MR15 and MR17 could not successfully amplify human STAT4.

The portion of the human STAT4 gene that was obtained by PCR was used to screen a Jurkat cell library prepared in the following manner: Jurkat T cells were grown in RPMI+ 10% fetal bovine serum. Total RNA was isolated according to the Guanidinium-HCl method (Chomczynski and Sacchi, 1987. Anal. Biochem. 162, 156–159.). Poly-A+RNA was purified using oligo-dT magnetic beads (Promega). Random primed and oligo-dT primed libraries were prepared. The cDNA libraries were constructed in the vector Lambda ZAPII (Stratagene) according to the protocol supplied by the manufacturer. The cDNA was size selected for greater than 1 kb by electrophoresis a on 5% polyacrylamide gel prior to ligation. Each library contained approximately $2 \times 10^6$ recombinant clones.

The STAT4 PCR fragment was labeled by random priming and hybridized in 1M NaCl, 50 mM Tris pH 7.4, 2 mM EDTA, 10× Denhardt's, 0.05% SDS, and 50 mg/ml salmon sperm DNA at 65° C. The filters were washed first in 2× SSC, 0.1% SDS, and then in 0.2× SSC, 0.1% SDS at 65° C. Eight cross-hybridizing clones were identified after screening $1\times10^6$ recombinants. Hybridizing clones were purified and converted into Bluescript plasmid DNA clones. The three largest clones were chosen for sequence analysis. The DNA sequence was determined using thermal cycle sequencing and the Applied Biosystems 373A sequencer. These cDNAs were determined to be identical at their 3' ends and variable in length at the 5' ends. The sequence reported here is from the longest of the cDNA clones.

EXAMPLES

1. Protocol for hStat 4 - IL-12 Receptor-peptide binding assay.

A. Reagents:

Neutralite Avidin: 20 µg/ml in PBS.

Blocking buffer: 5% BSA, 0.5% Tween 20 in PBS; 1 hr. RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P hStat 4 10× stock: $10^{-8}$–$10^{-6}$M "cold" hStat 4 inactive (not tyrphosporylated) and truncated (SH2 domain) hStat 4 supplemented with 200,000–250,000 cpm of labeled, inactive and truncated hStat 4 (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

IL-12-receptor-peptides: $10^{-8}$–$10^{-5}$M of each IL-12 receptor biotinylated peptides in PBS.

B. Preparation of assay plates:

Coat with 120 µl of stock N-Avidin per well overnight at 4° C.

Wash 2× with 200 µl PBS.

Block with 150 µl of blocking buffer.

Wash 2× with 200 µl PBS.

C. Assay:

Add 40 µl assay buffer/well.

Add 10 µl compound or extract.

Add 10 µl $^{33}$P-hStat 4 (20,000–25,000 cpm/o. 1–10 pmoles/well=$10^{-9}$–$10^{-7}$M final concentration).

Shake at 25C. for 15 min.

Incubate additional 45 min. at 25C.

Add 40 µl IL-12 receptor peptide mixture (0.1–10 pmoles/ 40 ul in assay buffer)

Incubate 1 hr at RT.

Stop the reaction by washing 4× with 200 µl PBS.

Add 150 µl scintillation cocktail.

Count in Topcount.

D. Controls for all assays (located on each plate):

a. Non-specific binding (no receptor peptide added)

b. Soluble (non-biotinylated receptor peptide) at 80% inhibition.

2. Protocol for hStat 4—DNA binding assay.

A. Reagents:

Neutralite Avidin: 20 µg/ml in PBS.

Blocking buffer: 5% BSA, 0.5% Tween 20 in PBS; 1 hr. RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P hStat 4 10× stock: $10^{-6}$–$10^{-8}$M "cold" hStat 4 supplemented with 200,000–250,000 cpm of labeled hStat 4 (Beckman counter). Place in the 4° C. microfridge during screening.

Protease inhibitor cocktail (1000×): 10 mg Trypsin Inhibitor (MB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Oligonucleotide stock: (specific biotinylated). Biotinylated oligo at 17 pmole/µl, hStat 4 binding site: (BIOTIN)-GTATTTCCCAGAAAAGGAAC (SEQUENCE ID NO: 3)

B. Preparation of assay plates:

Coat with 120 µl of stock N-Avidin per well overnight at 4° C.

Wash 2× with 200 µl PBS.

Block with 150 µl of blocking buffer.

Wash 2× with 200 µl PBS.

C. Assay:

Add 40 µl assay buffer/well.

Add 10 µl compound or extract.

Add 10 µl $^{33}$P-hStat 4 (20,000–25,000 cpm/0.1–10 pmoles/well=$10^{-9}$–$10^{-7}$M final concentration).

Shake at 25C. for 15 min.

Incubate additional 45 min. at 25C.

Add 40 µl oligo mixture (1.0 pmoles/40 ul in assay buffer with 1 ng of ss-DNA)

Incubate 1 hr at RT.

Stop the reaction by washing 4× with 200 µl PBS.

Add 150 µl scintillation cocktail.

Count in Topcount.

D. Controls for all assays (located on each plate):

a. Non-specific binding (no oligo added)

b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid encoding a human signal transducer and activator of transcription 4 (hStat 4) protein comprising the amino acid sequence of SEQ ID NO:2 or a fragment thereof having an hStat 4-specific binding affinity, wherein the fragment of SEQ ID NO:2 comprises at least one of residue 40, 45, 123, 148, 184, 189, 190, 220, 221, 229, 232, 240, 274, 280, 295, 298, 300, 304, 332, 381, 387, 409, 411, 413, 443, 488, 489, 492, 513, 516, 527, 529, 547, 574, 614, 617, 712, 724 and 742.

2. An isolated nucleic acid according to claim 1, wherein the fragment of SEQ ID NO:2 comprises residue 40.

3. An isolated nucleic acid according to claim 1, wherein the fragment of SEQ ID NO:2 comprises residue 45.

4. An isolated nucleic acid according to claim 1, wherein the fragment of SEQ ID NO:2 comprises residue 123.

5. An isolated nucleic acid according to claim 1, wherein the fragment of SEQ ID NO:2 comprises residue 148.

6. An isolated nucleic acid according to claim 1, wherein the fragment of SEQ ID NO:2 comprises residue 184.

7. An isolated nucleic acid according to claim 1, wherein the fragment of SEQ ID NO:2 comprises residue 189.

8. An isolated nucleic acid according to claim 1, wherein the fragment of SEQ ID NO:2 comprises residue 190.

9. An isolated nucleic acid according to claim 1, wherein the fragment of SEQ ID NO:2 comprises residue 220.

10. An isolated nucleic acid according to claim 1, wherein the fragment of SEQ ID NO:2 comprises residue 221.

11. An isolated nucleic acid according to claim 1, wherein the fragment of SEQ ID NO:2 comprises residue 229.

12. An isolated nucleic acid according to claim 1, wherein the fragment of SEQ ID NO:2 comprises residue 232.

13. An isolated nucleic acid according to claim 1, wherein the fragment of SEQ ID NO:2 comprises residue 240.

14. An isolated nucleic acid according to claim 1, wherein the fragment of SEQ ID NO:2 comprises residue 274.

15. An isolated nucleic acid according to claim 1, wherein the fragment of SEQ ID NO:2 comprises residue 280.

16. An isolated nucleic acid according to claim 1, wherein the fragment of SEQ ID NO:2 comprises residue 295.

17. An isolated nucleic acid according to claim 1, wherein the fragment of SEQ ID NO:2 comprises residue 298.

18. An isolated nucleic acid according to claim 1, wherein the fragment of SEQ ID NO:2 comprises residue 300.

19. An isolated nucleic acid according to claim 1, wherein the fragment of SEQ ID NO:2 comprises residue 304.

20. An isolated nucleic acid according to claim 1, wherein the fragment of SEQ ID NO:2 comprises residue 332.

21. An isolated nucleic acid according to claim 1, wherein the fragment of SEQ ID NO:2 comprises residue 381.

22. An isolated nucleic acid according to claim 1, wherein the fragment of SEQ ID NO:2 comprises residue 387.

23. An isolated nucleic acid according to claim 1, wherein the fragment of SEQ ID NO:2 comprises residue 409.

24. An isolated nucleic acid according to claim 1, wherein the fragment of SEQ ID NO:2 comprises residue 411.

25. An isolated nucleic acid according to claim 1, wherein the fragment of SEQ ID NO:2 comprises residue 413.

26. An isolated nucleic acid according to claim 1, wherein the fragment of SEQ ID NO:2 comprises residue 443.

27. An isolated nucleic acid according to claim 1, wherein the fragment of SEQ ID NO:2 comprises residue 488.

28. An isolated nucleic acid according to claim 1, wherein the fragment of SEQ ID NO:2 comprises residue 489.

29. An isolated nucleic acid according to claim 1, wherein the fragment of SEQ ID NO:2 comprises residue 492.

30. An isolated nucleic acid according to claim 1, wherein the fragment of SEQ ID NO:2 comprises residue 513.

31. An isolated nucleic acid according to claim 1, wherein the fragment of SEQ ID NO:2 comprises residue 516.

32. An isolated nucleic acid according to claim 1, wherein the fragment of SEQ ID NO:2 comprises residue 527.

33. An isolated nucleic acid according to claim 1, wherein the fragment of SEQ ID NO:2 comprises residue 529.

34. An isolated nucleic acid according to claim 1, wherein the fragment of SEQ ID NO:2 comprises residue 547.

35. An isolated nucleic acid according to claim 1, wherein the fragment of SEQ ID NO:2 comprises residue 574.

36. An isolated nucleic acid according to claim 1, wherein the fragment of SEQ ID NO:2 comprises residue 614.

37. An isolated nucleic acid according to claim 1, wherein the fragment of SEQ ID NO:2 comprises residue 617.

38. An isolated nucleic acid according to claim 1, wherein the fragment of SEQ ID NO:2 comprises residue 712.

39. An isolated nucleic acid according to claim 1, wherein the fragment of SEQ ID NO:2 comprises residue 724.

40. An isolated nucleic acid according to claim 1, wherein the fragment of SEQ ID NO:2 comprises residue 742.

* * * * *